United States Patent
Kyvik et al.

(10) Patent No.: US 8,251,957 B2
(45) Date of Patent: Aug. 28, 2012

(54) CATHETER SECUREMENT DEVICE

(75) Inventors: Kurt Kyvik, Ocala, FL (US); Scott Ryan, Ocala, FL (US); Arthur Parkhurst, Ocala, FL (US)

(73) Assignee: Zefon International, Inc., Ocala, FL (US)

( * ) Notice: Subject to any disclaimer, the term of this patent is extended or adjusted under 35 U.S.C. 154(b) by 165 days.

(21) Appl. No.: 12/924,776

(22) Filed: Oct. 5, 2010

(65) Prior Publication Data

US 2012/0083743 A1    Apr. 5, 2012

(51) Int. Cl.
*A61M 5/32* (2006.01)
(52) U.S. Cl. .................................. 604/180; 604/174
(58) Field of Classification Search .................. 604/174, 604/180, 179; 128/DIG. 6, DIG. 26
See application file for complete search history.

(56) References Cited

U.S. PATENT DOCUMENTS

| | | | |
|---|---|---|---|
| 4,702,736 A * | 10/1987 | Kalt et al. ...................... 604/180 |
| 4,838,868 A | 6/1989 | Forgar et al. |
| 5,147,322 A * | 9/1992 | Bowen et al. .................. 604/180 |
| 5,282,791 A | 2/1994 | Lipton et al. |
| 5,380,294 A * | 1/1995 | Persson ......................... 604/180 |
| 5,685,859 A | 11/1997 | Kornerup |
| 6,273,873 B1 | 8/2001 | Fleischer |
| D492,411 S | 6/2004 | Bierman |
| 7,137,968 B1 | 11/2006 | Burrell et al. |
| 7,637,894 B2 | 12/2009 | Fleischer |
| D608,444 S | 1/2010 | Kyvik et al. |
| D608,887 S | 1/2010 | Kyvik et al. |
| 7,648,485 B2 | 1/2010 | Fleischer |
| 8,162,898 B1 * | 4/2012 | Wright ........................... 604/180 |

* cited by examiner

*Primary Examiner* — Kevin C Sirmons
*Assistant Examiner* — Emily Schmidt
(74) *Attorney, Agent, or Firm* — Thomas C. Saitta

(57) ABSTRACT

A catheter securement device that adheres to the skin of a patient having an epidural catheter or similar small flexible tube member inserted percutaneously, the securement device having a flexible, sheet-like main body member capable of adhering to the skin of the patient, a notched pad member over which the catheter is bent, an exposed portion of adhesive to contact the catheter, and a releasable retention member to secure the catheter onto the main body member.

14 Claims, 3 Drawing Sheets

CATHETER SECUREMENT DEVICE

BACKGROUND OF THE INVENTION

This invention relates generally to the field of medical devices referred to as catheter securement devices, a catheter being defined herein to include a small diameter, flexible tube that is inserted through a person's skin and into a vein to deliver or remove fluids such as blood, saline solutions, medications, etc. A catheter securement device typically comprises a flexible sheet member adhesively adhered to the patient's skin, the device having means to retain the catheter tubing or a catheter housing, often a coupling or junction member for connecting one tube to another or to multiple tubes, in a relatively stable manner such that it is less likely for the catheter to be accidentally pulled from the patient.

Catheter securement devices are often located a short distance from the insertion site, such that the securement device has a minimal or reduced effect in securing the catheter tube in place at the actual insertion site. It is an object of this invention to provide a catheter securement device that reduces the likelihood of accidental dislodgement of the catheter by providing a structure that allows the securement device to be located close to or at the insertion site.

SUMMARY OF THE INVENTION

The invention is a catheter securement device adapted to be adhesively adhered to the skin of a patient, the device comprising a flexible sheet-like main body member, a lower adhesive layer disposed on the underside of the main body member, an upper adhesive layer disposed on the upper side of the main body member, a flexible sheet, flap or strap catheter retention member mounted to the upper side of the main body member by a portion of the upper adhesive layer, the flexible retention member having a fixed end and a releasable end, and a notched catheter pad member also mounted on the upper side of the main body member, preferably utilizing the upper adhesive layer. The retention member and pad member are arranged such that the retention member overlays the pad member. Each of the upper adhesive layer, main body member and lower adhesive layer comprise an edge recess in the area of the pad notch, such that there is no adhesive on a portion of the pad lower surface surrounding the notch. There is no adhesive at all on the pad upper surface.

The catheter securement device is adhered to the patient such that the notch is positioned adjacent or near the catheter insertion site. The catheter is brought up through the notch and positioned transversely across the main body member. The flexible retention member is then brought over the catheter and secured, the retention member pressing the catheter into an exposed portion of the upper adhesive layer. The flexible retention member may be releasably fastened utilizing the upper adhesive layer, or the flexible retention member may be held in closed position by a hook assembly member, the hook assembly member and the retention member combining to form a hook-and-loop-type fastener. The retention member may also be formed of a transparent or translucent material to enable visual inspection of the retained catheter. The pad member is preferably composed of a foam material.

DETAILED DESCRIPTION OF THE INVENTION

Figure 1:
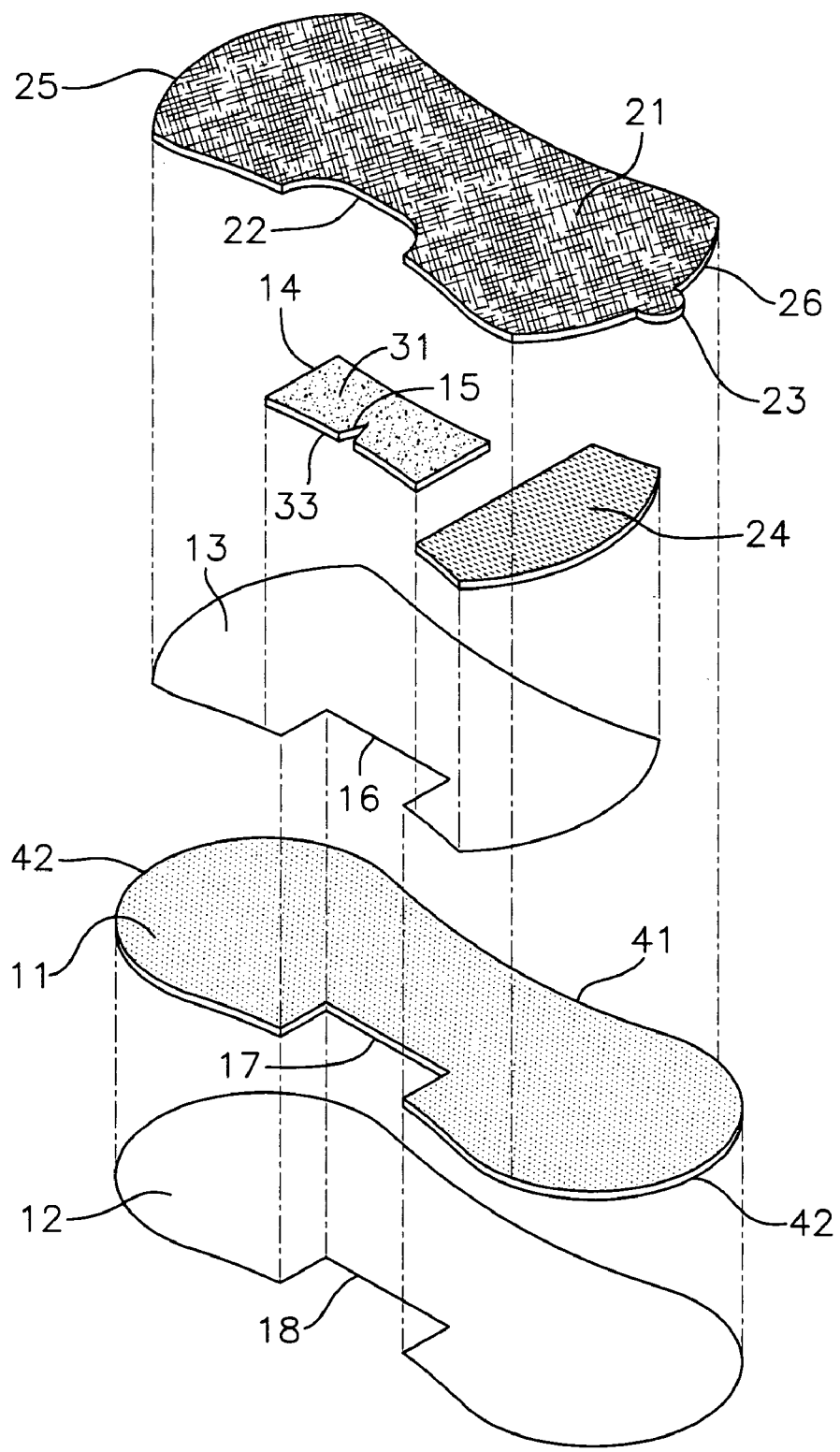
FIG. 1 is an expanded view of an embodiment of the catheter securement device.

With reference to the drawings, the invention will now be described in detail with regard for the best mode and the preferred embodiment. In general, the invention is a catheter securement device that adheres to the skin of a patient having an epidural catheter or similar small flexible tube member inserted percutaneously, the securement device acting to secure and retain the catheter to prevent or reduce movement near the insertion site or accidental dislodgement of the catheter. The securement device in general comprises a flexible, sheet-like main body member capable of adhering to the skin of the patient, a notched pad member over which the catheter is bent, and releasable retention member to secure the catheter onto the main body member.

The catheter sucurement device comprises a main body member 11. The main body member 11 is a flexible, thin, sheet-like member, generally elongated preferably into a dog-bone-style configuration with two sides 41, preferably concave, and two ends 42, preferably rounded, the main body member 11 being shorter in transverse or lateral direction than in the longitudinal direction. The main body member 11 is preferably formed of a synthetic fabric material. A main body member edge recess 17, shown as generally rectangular in configuration, is centered on one of sides 41. The edge recess 17 may have alternative perimeter configurations as well.

A lower adhesive layer 12, preferably composed of a hypoallergenic pressure sensitive adhesive (PSA), is disposed on the underside of main body member 11, and most preferably covers the entire underside of main body member 11. Because of the main body member edge recess 17, the lower adhesive layer 12 will have a corresponding lower adhesive edge recess 18. The lower adhesive layer 12 is chosen from the class of adhesives which are suitable to removably adhere the main body member 11 to the skin of the patient.

An upper adhesive layer 13, preferably composed of a hypoallergenic pressure sensitive adhesive (PSA), is disposed on the upper side of main body member 11, and preferably does not cover the entire upper surface of the main body member 11 such that portions of the main body member 11 adjacent the ends 42 are not covered with adhesive. Most preferably, the upper adhesive layer 13 extends completely across the main body member 11 in the transverse or lateral direction, i.e., from one side 41 to the other side 41. An upper adhesive layer edge recess 16 corresponds to the main body member edge recess 17.

Figure 4:
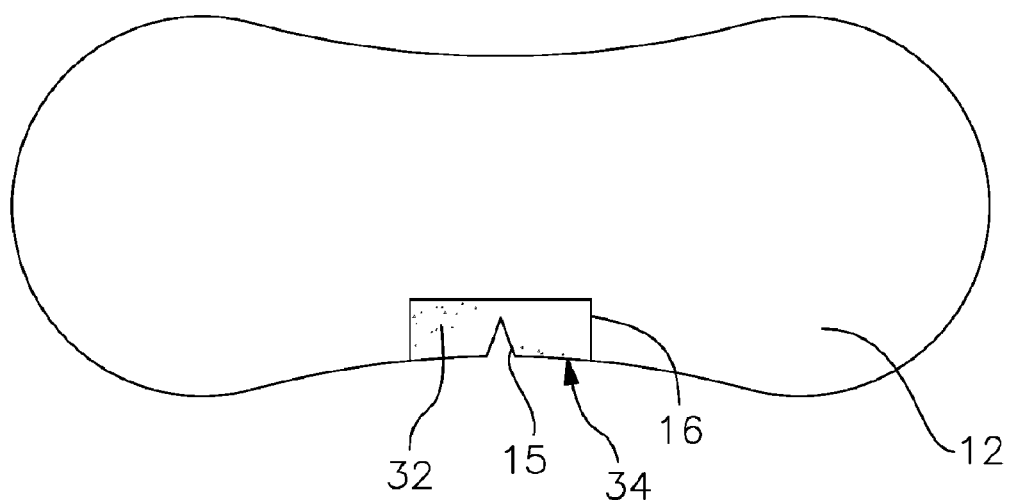
FIG. 4 is a bottom view of the device of FIG. 1.

A catheter pad member 14 is adhered to the upper surface of the main body member 11 utilizing a portion of the upper adhesive layer 13. The pad member 14 is preferably composed of a compressible synthetic foam material. The pad member 14 comprises an upper surface 31, a lower surface 32 and an exposed edge 33. The pad member 14 is mounted onto the main body member 11 such that the pad exposed edge 33 is positioned at the side 41 of the main body member 11 at the location of the main body member edge recess 17 and upper adhesive edge recess 16. The pad member 14 is wider and longer than the main body member edge recess 17 and upper adhesive edge recess 16, such that a portion of the upper adhesive layer 13 will adhere to the pad lower surface 32 along the three interior edges of the pad member 14. In this manner the lower adhesive layer edge recess 18, the main body member edge recess 17 and the upper adhesive edge recess 16 define a lower exposed region 34 on the pad lower surface 32 having no adhesive, as seen in FIG. 4. The lower exposed region 34 encompasses the notch member 15. The pad upper surface 31 has no adhesive. The transverse width of the pad member 14 is shorter than the transverse width of the main body member 11, and preferably the width of the pad member 14 is less than half the width of the main body member 11. In this manner an exposed region 19 of the upper adhesive layer 13 is presented, which as will be described later is one component to secure the catheter 99 against undesirable movement.

The pad member 14 further comprises a notch 15 disposed in the exposed edge 33. The notch extends a short distance transversely toward the interior of the pad member 14. Preferably the notch 15 has an open volume in the longitudinal and transverse direction with a generally V-shaped open interior, although other shapes such as circular, oblong, rounded, etc. are suitable alternatives.

Connected to the main body by a portion of the upper adhesive layer 13 is a thin, flexible catheter retention member 21 in the form of a sheet, flap or strap. The retention member 21 has a fixed end 25 and a releasable end 26, the retention member 21 being positioned such that in a closed position it overlaps catheter pad member 14 and upper adhesive layer exposed region 19. The retention member 21 preferably is shorter in the longitudinal direction that the main body member 11 and preferably is generally equal in width to the main body member 11. One side of the retention member 21 is provided with a recess 22 corresponding in size and location to the main body member edge recess 17. The catheter retention member 21 may also be provided with a tab member 23 on its releasable end 26 for easier closing and opening. The retention member is preferably composed of a synthetic fabric material, and in alternative embodiments the retention member 21 may have a transparent window or be made of transparent material in order to provide visual access to the retained catheter 99 without need for releasing the retention member 21.

Figure 2:
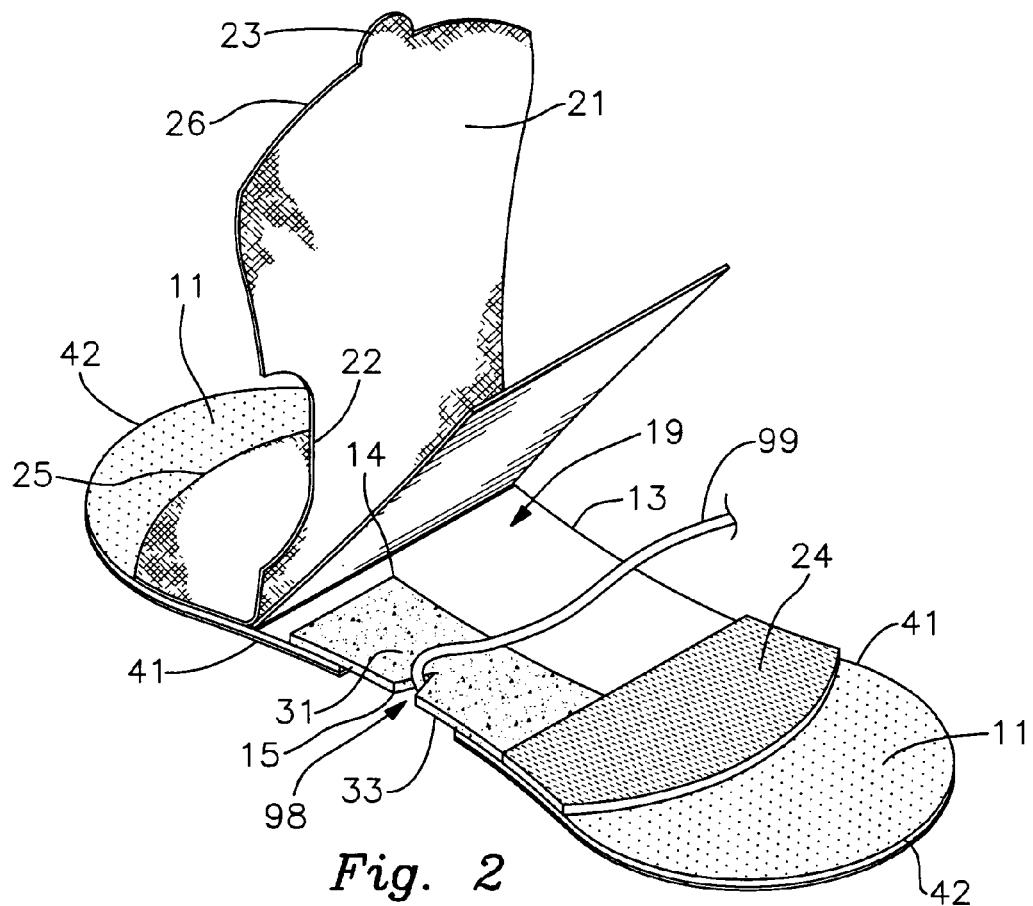
FIG. 2 is a perspective view of the device of FIG. 1, shown in the use position prior to closure of the catheter retention member.
Figure 3:
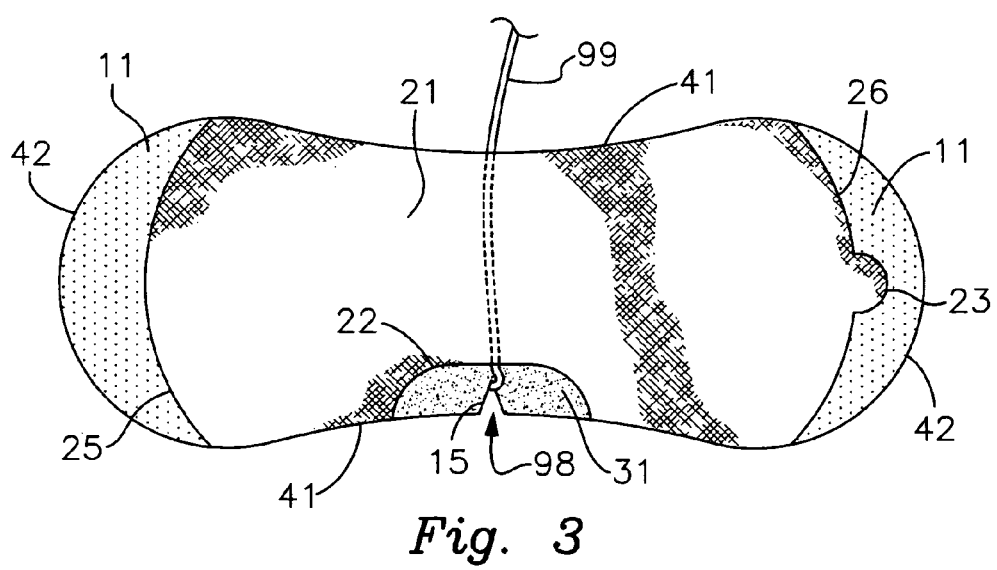
FIG. 3 is a top view of the device of FIG. 2, shown in the use position after closure of the catheter retention member to secure the catheter.
Figure 5:
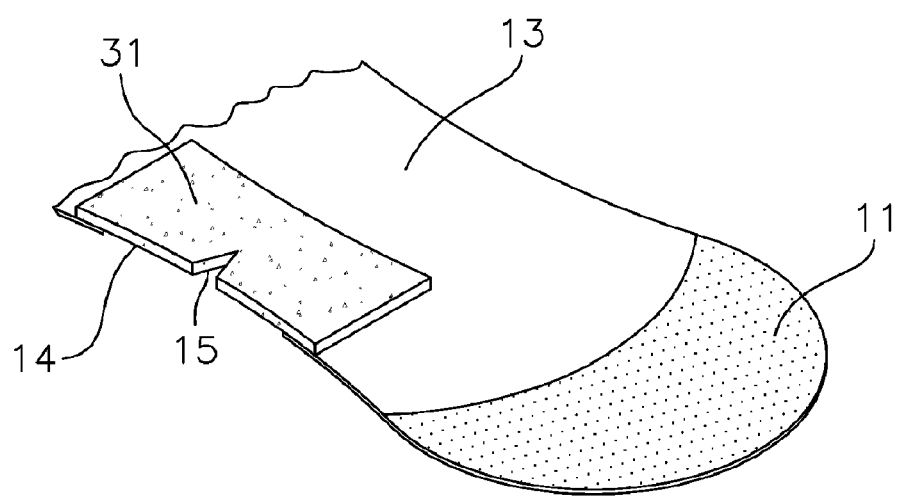
FIG. 5 is a partial view of an alternative embodiment of the catheter securement device, showing the use of the upper adhesive layer to releasably retain the retention member.

In the embodiment depicted in FIGS. 1-2, the catheter securement device is further provided with a hook assembly member 24 mounted onto the main body member 11 by a portion of the upper adhesive layer 13. The hook assembly member 24 is positioned on the opposite side of the pad member 14 from the fixed end 25 of the retention member 21. The hook assembly member 24 and the underside of the releasable end 26 of the retention member 21 together form a hook-and-loop-type fastener. In an alternative embodiment shown in FIG. 5, no hook assembly member 24 is present, and the underside of the releasable end 26 of the retention member 21 makes direct contact with a portion of the upper adhesive layer 13.

For use the catheter securement device is packaged with release layers positioned on the exposed adhesive surfaces, the release layers being removed for use, as is well known in the art. The catheter securement device is adhered to the patient's skin such that the main body 15 is located at or adjacent the catheter insertion site 98, such that the catheter 99 extends upwardly through the notch member 15. The catheter 99 is then bent sideways or backwards to extend transversely across the main body member 11 above the pad member 14 and pressed into the upper adhesive layer exposed region 19, as shown in FIG. 2. The retention member 21 is then brought down snuggly across the catheter member 99 and its releasable end 26 is temporarily secured to the main body member 11 utilizing the hook assembly member 24, as in FIG. 2, or a portion of the upper adhesive layer 13, as in FIG. 5. The retention member 21 maintains the catheter in contact with the pad upper surface 31 and the upper adhesive layer exposed region 19, thereby securing the catheter 99 in a controlled manner.

Because there is no adhesive on the pad upper surface 31 or on the pad lower exposed region 34, the compressible pad member 14 can shift slightly or be compressed to provide for a comfortable securement and to accommodate slight movement of the catheter 99, as does the open interior area of notch member 15. Were the pad lower surface covered completely by lower adhesive layer 12, such movement would be restricted because pad member 15 would be completely adhered to the patient's skin. Likewise, the presence of the body member edge recess 17 and the retention member recess 22 increase comfort to the patient by not compressing the catheter 99 at the bending region.

It is to be understood that equivalents and substitutions to elements and structures set forth above, which are not intended to be limiting unless necessary for patentability, may be obvious to those of ordinary skill in the art, and therefore the true scope and definition of the invention is to be as set forth in the following claims.

We claim:

1. A catheter securement device comprising:
   a thin, flexible main body member comprising two sides, two ends, an upper side, an underside, and an edge recess disposed on one of said sides;
   a lower adhesive layer disposed on the underside of said main body member;
   an upper adhesive layer disposed on the upper side of said main body member;
   a pad member mounted onto said main body member, said pad member comprising a notch member, a pad upper surface and a pad lower surface, said pad upper surface having no adhesive, said pad lower surface having a pad lower exposed region having no adhesive, said pad lower exposed region being smaller than said pad lower surface, wherein said notch member is positioned over said main body member edge recess and encompassed by said pad lower exposed region;
   a retention member comprising a fixed end mounted onto said main body member, a retention member recess corresponding in location to said main body edge recess, and a releasable end, said releasable end being releasably joined to said main body member on the opposite side of said pad member from said fixed end;
   wherein said pad member has a shorter width than said main body member, such that an exposed region of said upper adhesive layer is defined beneath said retention member.

2. The device of claim 1, further comprising a hook assembly member mounted on said upper side of said main body member by a portion of said upper layer adhesive, said releasable end of said retention member being releasably joined to said main body member by said hook assembly member.

3. The device of claim 1, wherein said main body sides are concave and said main body ends are rounded.

4. The device of claim 1, wherein said lower adhesive layer covers the entire said underside of said main body member, and wherein said upper adhesive layer covers only a portion of said upper side of said main body member, such that the portion of said upper side of said main body member adjacent said main body ends are not covered by adhesive.

5. The device of claim 1, wherein said retention member is transparent.

6. The device of claim 1, wherein said releasable end of said retention member is releasably joined to said main body member by a portion of said upper adhesive layer.

7. The device of claim 1, wherein said notch member has an open interior.

8. A catheter securement device comprising:
   a thin, flexible main body member comprising two sides, two ends, an upper side, an underside and an edge recess disposed on one of said sides;
   a lower adhesive layer disposed on the underside of said main body member;
   an upper adhesive layer disposed on the upper side of said main body member;
   a pad member mounted onto said main body member by a portion of said upper adhesive layer, said pad member comprising a pad upper surface, a pad lower surface, a pad exposed edge and a notch member disposed in said pad exposed edge, said notch member having an open interior, said pad member being larger than said main body edge recess, said pad upper surface having no adhesive, said pad lower surface having a pad lower exposed region having no adhesive and encompassing said notch member, said pad lower exposed region being smaller than said pad lower surface, wherein said pad member and said notch member are positioned over said main body member edge recess;
   a retention member comprising a fixed end mounted onto said main body member, a retention member recess corresponding in location to said main body edge recess, and a releasable end, said releasable end being releasably joined to said main body member on the opposite side of said pad member from said fixed end;
   wherein said pad member is less than half the width of said main body member, such that an exposed region of said upper adhesive layer is defined beneath said retention member.

9. The device of claim 8, further comprising a hook assembly member mounted on said upper side of said main body member by a portion of said upper layer adhesive, said releasable end of said retention member being releasably joined to said main body member by said hook assembly member.

10. The device of claim 8, wherein said main body sides are concave and said main body ends are rounded.

11. The device of claim 8, wherein said lower adhesive layer covers the entire said underside of said main body member, and wherein said upper adhesive layer covers only a portion of said upper side of said main body member, such that the portion of said upper side of said main body member adjacent said main body ends are not covered by adhesive.

12. The device of claim 8, wherein said retention member is transparent.

13. The device of claim 8, wherein said releasable end of said retention member is releasably joined to said main body member by a portion of said upper adhesive layer.

14. A catheter securement device comprising:
   a thin, flexible main body member comprising two concave sides, two rounded ends, an upper side, an underside and an edge recess disposed on one of said sides;
   a lower adhesive layer disposed on the underside of said main body member;
   an upper adhesive layer disposed on the upper side of said main body member;
   a pad member mounted onto said main body member by a portion of said upper adhesive layer, said pad member comprising a pad upper surface, a pad lower surface, a pad exposed edge and a notch member disposed in said pad exposed edge, said notch member having an open interior, said pad member being larger than said main body edge recess, said pad upper surface having no adhesive, said pad lower surface having a pad lower exposed region having no adhesive and encompassing said notch member, said pad lower exposed region being smaller than said pad lower surface, wherein said pad member and said notch member are positioned over said main body member edge recess;
   a retention member comprising a fixed end mounted onto said main body member and a releasable end, said releasable end being releasably joined to said main body member on the opposite side of said pad member from said fixed end;
   a hook assembly member mounted on said upper side of said main body member by a portion of said upper layer adhesive, said releasable end of said retention member being releasably joined to said main body member by said hook assembly member;
   wherein said lower adhesive layer covers the entire said underside of said main body member, and wherein said upper adhesive layer covers only a portion of said upper side of said main body member, such that the portion of said upper side of said main body member adjacent said main body ends are not covered by adhesive;
   wherein said pad member has a shorter width than said main body member, such that an exposed region of said upper adhesive layer is defined beneath said retention member.

* * * * *